United States Patent
Ye et al.

(10) Patent No.: US 11,493,463 B2
(45) Date of Patent: Nov. 8, 2022

(54) DETERMINING BOREHOLE MUD COMPOSITION

(71) Applicant: Halliburton Energy Services, Inc., Houston, TX (US)

(72) Inventors: Xiangnan Ye, Cypress, TX (US); Dale E. Jamison, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 716 days.

(21) Appl. No.: 16/520,087

(22) Filed: Jul. 23, 2019

(65) Prior Publication Data
US 2021/0025840 A1    Jan. 28, 2021

(51) Int. Cl.
| | | |
|---|---|---|
| *G01N 25/18* | (2006.01) | |
| *G01N 33/28* | (2006.01) | |
| *E21B 49/08* | (2006.01) | |

(52) U.S. Cl.
CPC ............ *G01N 25/18* (2013.01); *E21B 49/08* (2013.01); *E21B 49/086* (2013.01); *E21B 49/0875* (2020.05); *G01N 33/2823* (2013.01); *G01N 33/2847* (2013.01)

(58) Field of Classification Search
CPC .... E21B 49/08; E21B 49/086; E21B 49/0875; G01N 25/18; G01N 33/2823; G01N 33/2847
USPC ......................................................... 374/44
See application file for complete search history.

(56) References Cited

U.S. PATENT DOCUMENTS

| | | |
|---|---|---|
| 9,939,553 B2 | 4/2018 | Jamison et al. |
| 2016/0319662 A1 | 11/2016 | Zuo et al. |
| 2018/0045044 A1 | 2/2018 | Ye et al. |

(Continued)

FOREIGN PATENT DOCUMENTS

KR          101593976 B1    2/2016

OTHER PUBLICATIONS

"Methods for Predicting Water-Based Drilling Fluids %Water and ASG Using Indirect Measurements"; PCT/US2019/041638; Jul. 12, 2019.

(Continued)

*Primary Examiner* — Nimeshkumar D Patel
*Assistant Examiner* — Jean F Morello
(74) *Attorney, Agent, or Firm* — Tenley Krueger; Parker Justiss, P.C.

(57) ABSTRACT

The disclosure presents a technique for predicting the composition of a borehole mud using a thermal conductivity parameter of the mud and a dilution liquid. The mud can be altered by conditions within the borehole, such as material, fluid, and temperature affecting the original mud composition pumped into the borehole location. The mud can be an oil-based, water-based, or another type of mud of a well system. The technique can extract a measured quantity of mud and place it into a mud container. A first thermal conductivity parameter can be calculated for the extracted mud. A dilution liquid can be mixed into the extracted mud in the mud container and a second thermal conductivity parameter calculation can be performed. From the calculated first and second thermal conductivity parameters, the composition of the mud, as well as the fractional proportions of the major components of the mud, can be predicted and computed.

20 Claims, 3 Drawing Sheets

(56) References Cited

U.S. PATENT DOCUMENTS

2018/0202246 A1 7/2018 Kleinguetl et al.
2021/0016297 A1* 1/2021 Birchfield ............... B04B 13/00

OTHER PUBLICATIONS

Cheng, et al.; "A technique for predicting the thermal conductivity of suspensions, emulsions and porous materials"; Int. J. Heat Mass Transfer.; vol. 13; 1970; pp. 537-546.
Lotfizadeh, et al.; "A continuum Maxwell Theory for the Thermal Conductivity of Clustered Nanocolloids"; J. Nanoparticle Research; vol. 17(6); May 29, 2015; 12 pgs.

* cited by examiner

DETERMINING BOREHOLE MUD COMPOSITION

TECHNICAL FIELD

This application is directed, in general, to determining mud composition and, more specifically, to determining mud composition in a well system.

BACKGROUND

In hydrocarbon well systems, a mud is often used to facilitate the drilling of the borehole or the extraction of hydrocarbons, such as with an injection well system. The original mud pumped into the borehole can be altered by various processes within the borehole, such as interactions with the hydrocarbons, other fluids in the borehole, entrainment of drill solids, and absorption by the surrounding subterranean formations. The altered mud may not maintain the properties or characteristics desired by the well system operators.

Currently, a retort process is typically used downhole to compute the altered mud composition. The altered mud composition can then be communicated to a well site controller or engineer for further analysis and adjustments, such as modifying the composition of the original mud as specified in the well site job plan. The retort process can take a significant amount of time to complete, such as thirty minutes or more. In addition, the loss of water during the process can skew the results. Cleaning the mud container after a retort can be problematic. A faster and more efficient means for determining the altered mud composition would be beneficial in reducing the processing time and allow for the determination process to run more frequently than with the retort process.

SUMMARY

In one aspect, a method to determine a composition of a mud in a well system is disclosed. In one embodiment, the method includes (1) obtaining a thermal conductivity measurement for a portion of the mud, (2) calculating a first thermal conductivity parameter, using the measurement of thermal conductivity for the portion of the mud, (3) creating a diluted mud by adding a dilution liquid to the portion of the mud, (4) calculating a second thermal conductivity parameter, using a measurement of thermal conductivity for the diluted mud, and (5) computing an ASG of the mud and a ratio of fractional components of the mud utilizing the first thermal conductivity parameter and the second thermal conductivity parameter.

In another aspect, a system to determine a composition of a mud from a well system is disclosed. In one embodiment, the system includes: (1) a first mud container, operable to hold the mud from the well system, (2) a dilution liquid dispenser, operable to dispense a measured volume of dilution liquid into the first mud container to form a diluted mud, (3) an agitator, operable to homogenize the diluted mud, (4) a probe, operable to measure a first thermal conductivity of contents of the first mud container, and calculate a first thermal conductivity parameter using the measured first thermal conductivity, and (5) a mud tool controller, operable to communicate with the first mud container, the dilution liquid dispenser, the agitator, and the probe, and operable to compute an ASG of the mud and a ratio of the fractional components of the mud, utilizing the first thermal conductivity parameter.

In a third aspect, a computer program product having a series of operating instructions stored on a non-transitory computer-readable medium that directs a data processing apparatus when executed thereby to perform operations to determine a composition of a mud within a borehole is disclosed. In one embodiment, the operations include: (1) calculating a first thermal conductivity parameter, using a measurement of thermal conductivity for a portion of the mud, (2) calculating a second thermal conductivity parameter, using a measurement of thermal conductivity for a diluted mud, wherein the diluted mud is created by adding a dilution liquid to the portion of the mud, and (3) computing an ASG of the mud and a ratio of fractional components of the mud utilizing the first thermal conductivity parameter and the second thermal conductivity parameter.

BRIEF DESCRIPTION

Reference is now made to the following descriptions taken in conjunction with the accompanying drawings, in which.

DETAILED DESCRIPTION

In many hydrocarbon well systems, a mud is used to facilitate the drilling of a borehole, where mud can be a drilling mud (such as oil or water based muds, where the oil can be a petroleum or synthetic based product), gaseous drilling fluids (such as air or other gases, by itself or combined with water, polymers, and other additives), water (such as sea water and other water compositions), and other types of fluids that can be utilized within the borehole. In drilling scenarios, for example, logging while drilling (LWD), measuring while drilling (MWD), and other types of well systems (see FIG. 1), the mud can contain the wellbore pressure, lubricate the bit, assist in the removal of drilled solids, and other uses. The mud is initially prepared to a specified formula or balance of materials. For example, the mud can include a base oil, a water, a low gravity solid (LGS), a high-gravity solid (HGS), and other additives. Water, as used herein, can be various water solutions or mixtures, such as distilled, filtered, ground water, tap water, brine, salinized, and water with other additives.

The mud is pumped from a storage location into the borehole of the well system. Once the mud is pumped into the borehole, the mud can interact with other fluids and hydrocarbons present in the borehole, and interact with the surrounding subterranean formation materials. Overtime, the characteristics of the mud can be altered by these other fluids and materials, for example, materials from the subterranean formation can be absorbed into the mud and part of the mud can be absorbed into the subterranean formation. In addition, the mud properties can be affected by the entrainment of drill solids and the accumulation of cutting fines. The borehole geometry can affect the mud characteristics as well. In addition, thermal changes within the borehole can affect the characteristics of the mud. Due to the changes of the mud characteristics, a well system job plan may need to be changed or the original mud composition may need to be altered to compensate for the changes occurring downhole.

Conventionally, drilling fluid properties are tested on the surface with test samples periodically taken from the active pit. Typically, a retort system and a salinity measurement process are used to measure oil to water ratio (OWR) and average specific gravity (ASG) of the drilling fluid. This method provides a distillation process of the mud from which the results can be analyzed to determine the composition of the mud as altered by the environment. A retort system can take up to 30 minutes or more to complete, and typically is not done more than four times in a 24-hour period. Retort results may have some content underreported due to the loss of water during the processing of the retort or the trapping of water in the condenser components. In addition, maintenance may be required on the retort system to clear trapped solids and to clean the mud container for the next testing cycle.

This disclosure demonstrates a method and system for determining the composition of mud, such as the original mud composition or the altered mud composition where the mud may have been altered by materials, fluids, and conditions in the borehole environment. The disclosed process uses thermal conductivity measurements to predict and compute the composition of the mud. The disclosed process can reduce the under or over report of water and oil content, and be completed in approximately two to five minutes, depending on the equipment being used.

The process can determine the mud composition within a margin of error of approximately +/−2.5% to +/−5.0% on OWR and volume fraction of the oil, water, and solids components. This compares equivalently or better to the conventional retort process that is typically not better than +/−5.0% margin of error. A compositional change resulting in ⅒ of a pound per gallon density difference downhole can lead to an approximate increase or decrease in the equivalent circulating density (ECD) margin of error by 0.7%.

In addition, the cleaning of the mud container can be less difficult than with the retort system, allowing a faster turn-around for the testing process. Therefore, additional mud composition computations can be performed within each 24-hour period, while improving the reliability of the results. The results of the process can be communicated to other well systems, for example, a well site controller. The well site controller can then adjust the well system job plan to improve the efficiency of the well system, such as adjusting the original mud composition prior to being pumped into the borehole. In addition, the results can be utilized to direct surface treatment methods such as centrifuges, shakers, and hydro cyclones.

Muds used within the well system are typically oil-based muds (OBM) and water-based muds (WBM), though other mud types, for example, the list above, can be utilized. The determination of the composition of mud can include the OWR and the ASG for OBM, and the ASG for WBM. In addition, the results of the composition testing of the mud can include the fractional share of the major components of the mud, such as the relative ratios of base oil, water, LGS, HGS, and other mud components.

For the following details, an OBM is being demonstrated, but the process can be applied to WBM and other types of muds. The thermal conductivity of a suspension can be calculated by an equation as demonstrated in Equation 1A.

$$TC = \sum_{i=1}^{4} f(TC_i, V_i) \quad \text{Equation 1A}$$

Example thermal conductivity of a suspension where $TC_i$ is the thermal conductivity of each of the four major components of the mud, $V_i$ is the volumetric fraction of each of the four major components of the mud, and i is the counter through the four major components of the mud.

For many mud formulations, the $TC_i$ can be determined previously, e.g., pre-computed, and can be stored in a data store for use by the process, such as a database located with the mud composition system.

For multiphase fluids, the bulk thermal conductivity and their respective volume percentages can be modeled by the base liquid as a continuous phase and the solids as a discontinuous phase. Equation 1B provides one example of such a model.

$$R_e = \frac{1}{\sqrt{C(k_c - k_d)[k_c + B(k_d - k_c)]}}$$

$$\ln \frac{\sqrt{[k_c + B(k_d - k_c)]} + \frac{B}{2}\sqrt{[C(k_c - k_d)]}}{\sqrt{[k_c + B(k_d - k_c)]} - \frac{B}{2}\sqrt{[C(k_c - k_d)]}} + \frac{1-B}{k_c} \quad \text{Equation 1B}$$

Example thermal conductivity using continuous and discontinuous phases where $k_c$ is the thermal conductivity of the continuous phase, $k_d$ is the thermal conductivity of the discontinuous phase, B and C are functions of the conventional discontinuous phase volumetric fraction $\phi_d$, as $$B = \sqrt{\frac{2}{3}\phi_d}, \text{ and } C = -\frac{4}{B}.$$

The thermal conductivity values $k_c$ and $k_d$ can be pre-determined, such as in a lab environment or on site of the well system. The thermal conductivity of the mixture can be shown as ($1/R_e$) which is represented as TC in Equation 1A. The thermal conductivity changes can be used with the original volumetric balance to find the new or changed volumetric balance.

The mass and volume of the mud components should balance as demonstrated in Equations 2 and 3.

$$\rho = \sum_{i=1}^{4} f(\rho_i, V_i) \quad \text{Equation 2}$$

Example mass of the mud components $$1 = \sum_{i=1}^{4} (V_i) \quad \text{Equation 3}$$

Example fractional volume balance of the mud components where $\rho_i$ is the density of each component of the mud, and $\rho$ is the total density.

Figure 2:
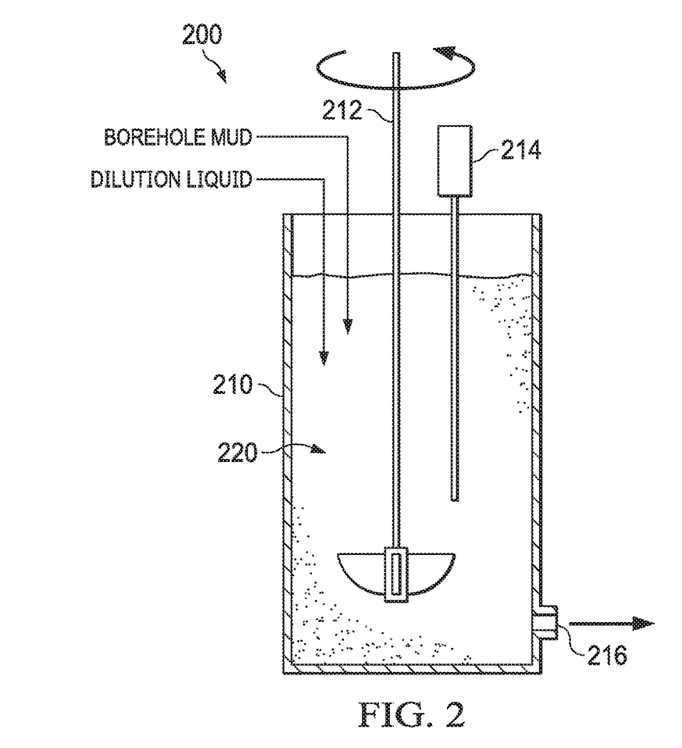
FIG. 2 is an illustration of a diagram of an example schematic functional view of a mud composition measurement system.
Figure 4:
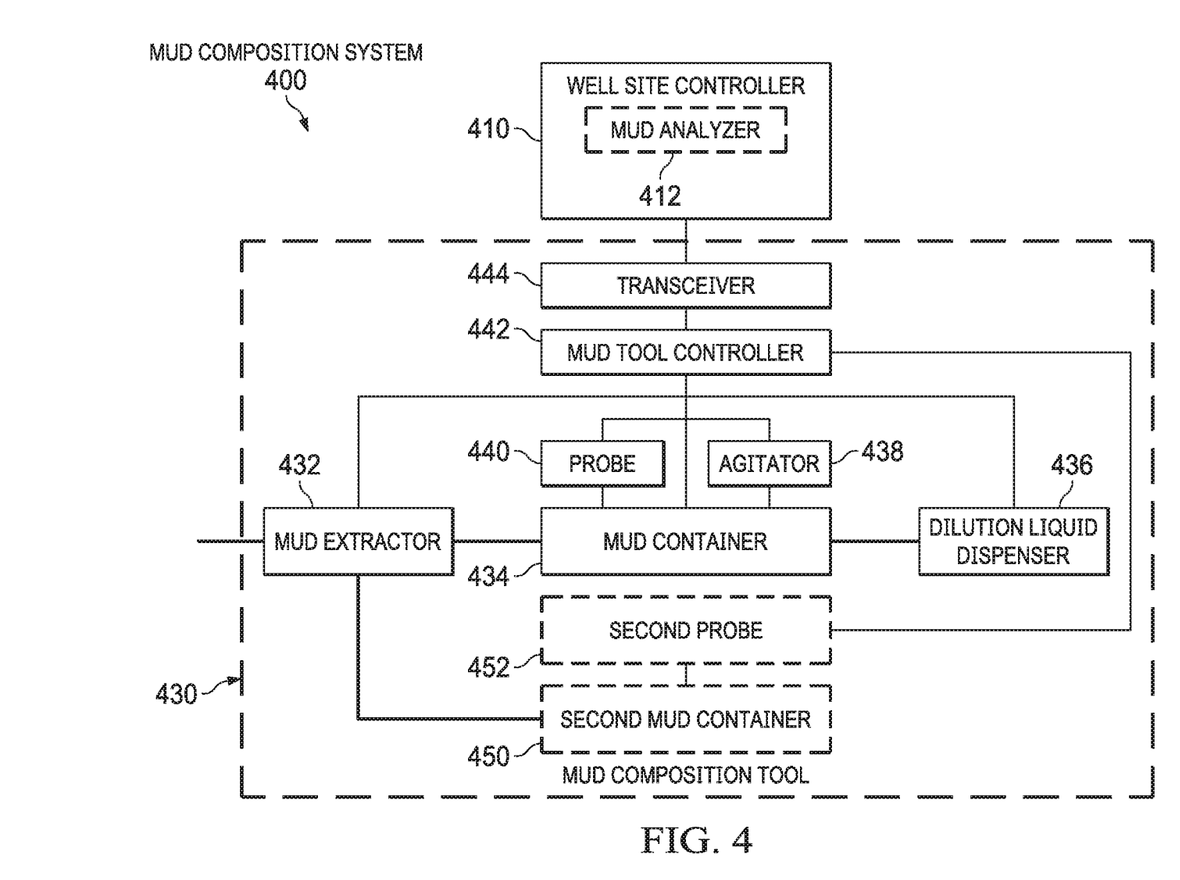
FIG. 4 is an illustration of a block diagram of an example mud composition system.

The thermal conductivity of the mud downhole can be calculated using a mud composition system as described in FIGS. 2 and 4. The testing process can calculate a thermal conductivity parameter and then can introduce a dilution liquid into the mud followed by a recalculation of the thermal conductivity parameter. The dilution liquid can be a base oil, a water, or another additive, such as an LGS or HGS. Alternatively, the dilution liquid can be a combination, such as a base oil and a water. Approximately 2.5% to 30.0% by volume of dilution liquid is added to the mud to form a diluted mud, with 5.0% to 20.0% being a typical range. The volume of the dilution liquid added can be lesser or greater than the range identified depending on the mud and dilution liquid characteristics, such as 1.0% or 50% by volume. Enough dilution liquid should be added to enable a measurable difference in thermal conductivity, while not enough to further alter the mud characteristics.

The dilution liquid can be mixed into the mud in a mud container using an agitator of various types. The agitation process should be performed just long enough to create a homogenized mixture, as continued agitation past this point may introduce additional thermal energy which could affect the results. The agitation process can be done for typically two minutes, and can be a shorter or longer time depending on the mud, the dilution liquid characteristics, and other factors, such as the equipment being utilized, such as one minute or ten minutes.

The thermal conductivity of the diluted mud can then be measured which is a function of the new composition of the diluted mud. Equation 4 demonstrates the thermal conductivity measurement for the diluted mud.

$$TC' = \sum_{i=1}^{4} f(TC_i, V'_i)$$

Equation 4

Example thermal conductivity measurement for diluted mud where $V'_i$ is the new volumetric fraction of each of the major components of the diluted mud utilizing the added dilution liquid. The dilution liquid is dispensed using a known and measured amount so that the dilution ratios are known. Equation 4 can also be structured to utilize the formulation from Equation 1B or other thermal conductivity models.

The new volumetric fraction can be computed as demonstrated in Equation 5 which uses the known and measured amount of dilution liquid to determine the new volume percentages.

Equation 5: Example volumetric fraction of the diluted mud after the introduction of the dilution liquid $$V'_i = f(V_i)$$

where the function $f$ can be represented by the following specific functions using, for example, an addition of 5.0% water by volume. If a different volume was added, or if base oil or solids were added, the various functions would be respectively modified to accommodate the differences.

$$F(V'_{water}) = (5.0\% + V_{water})/(5.0\% + 1),$$

$$F(V'_{oil}) = V_{oil}/(5.0\% + 1),$$

$$F(V'_{HGS}) = V_{HGS}/(5.0\% + 1), \text{ and}$$

$$F(V'_{LGS}) = V_{LGS}/(5.0\% + 1).$$

The functions of Equation 5 can be solved numerically using various methods, for example, Newtonian method, Secant method, Adomian decomposition method, and other numerical methods. In this disclosure, a nonlinear least squares approach has been used to ensure a global minimum error is obtained.

Figure 3:
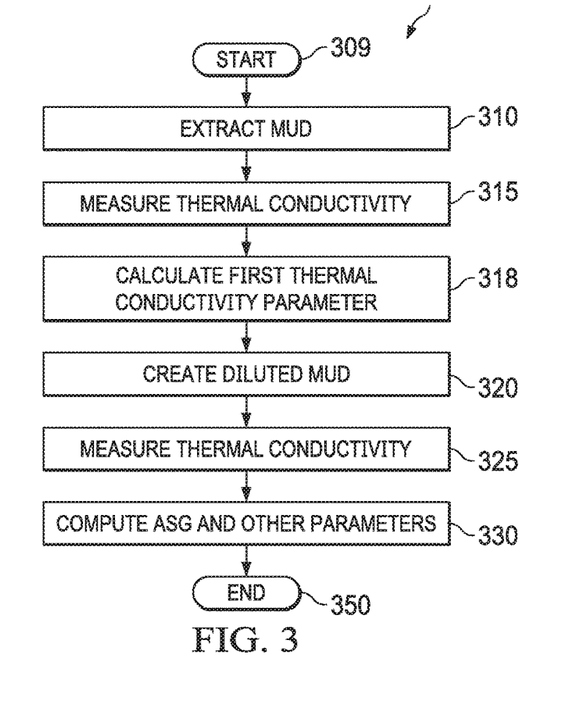
FIG. 3 is an illustration of a flow diagram of an example method for determining the composition of a mud.

The process for determining the mud composition of the mud can then follow the following steps, as further detailed in FIG. 3. A measured amount of mud, collected from a mud source, such as a downhole location, is put into a mud container. A thermal conductivity calculation to determine the first parameter TC is performed. The mud is diluted with a dilution liquid to form a diluted mud. A second thermal conductivity calculation is performed to determine the second parameter TC'. Subsequently, the composition of the altered mud can be determined, such as the OWR and ASG. Equation 6 demonstrates an algorithm to compute the OWR and Equation 7 demonstrates an algorithm to compute the ASG. Equations 6 and 7 can be utilized by a mud analyzer in executing the processes as described herein.

$$OWR = \frac{V_{oil}}{V_{oil} + V_{water}}$$

Equation 6

Example OWR computation $$ASG = \frac{\rho_{LGS} * V_{LGS} + \rho_{HGS} * V_{HGS}}{V_{LGS} + V_{HGS}}$$

Equation 7

Example ASG computation where $V_{oil}$ is the volumetric fraction of the base oil,
$V_{water}$ is the volumetric fraction of the water,
$\rho_{LGS}$ is the density of the LGS component,
$V_{LGS}$ is the volumetric fraction of the LGS component,
$\rho_{HGS}$ is the density of the HGS component, and
$V_{HGS}$ is the volumetric fraction of the HGS component.

Figure 1:
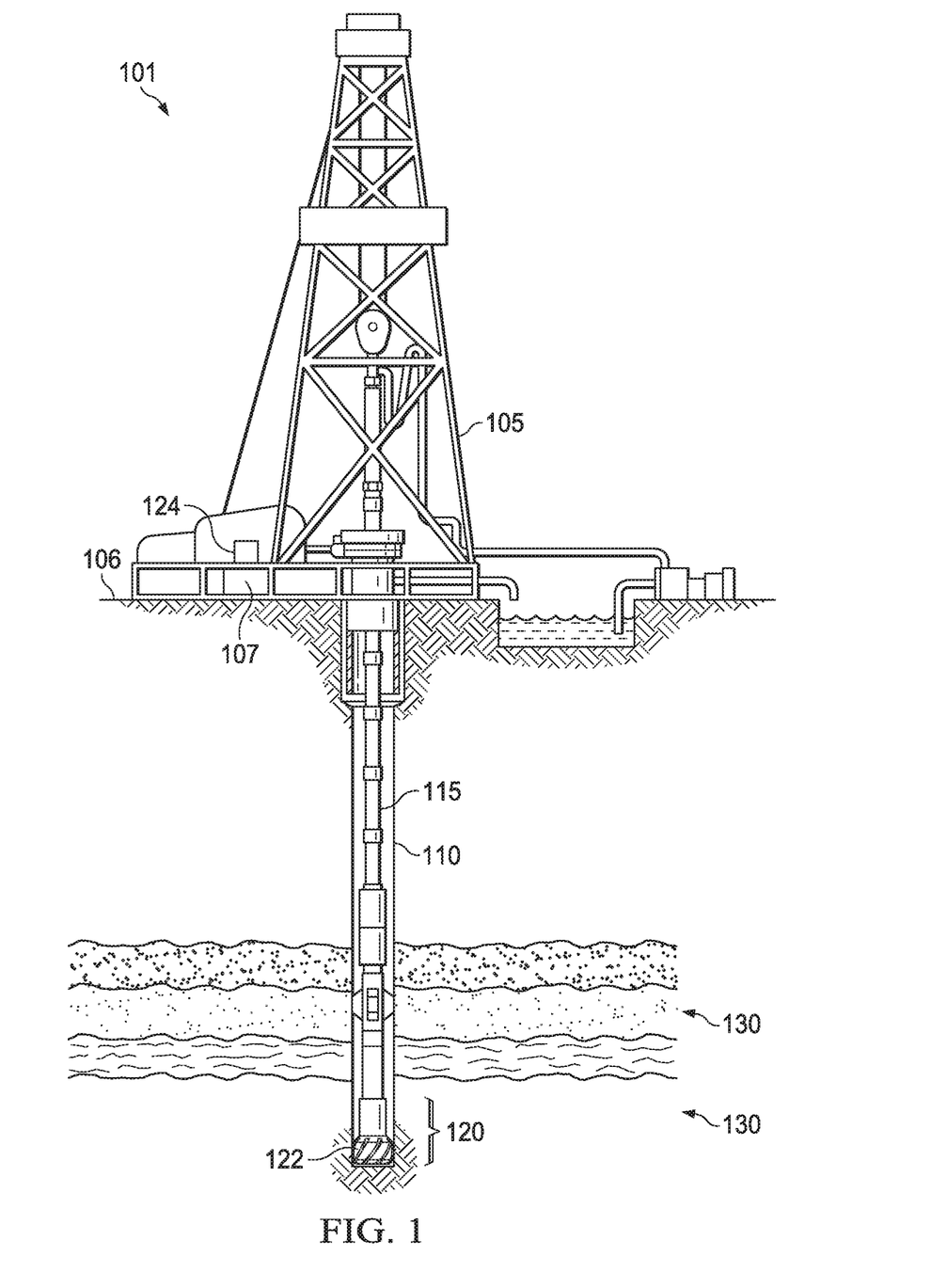
FIG. 1 is an illustration of a diagram of an example logging while drilling well system.

Turning now to the figures, FIG. 1 is an illustration of a diagram of an example well system 101, for example, a LWD or MWD well system. Well system 101 includes a derrick 105 supporting drill string 115, and well site controller 107. Well site controller 107 includes a processor and a memory and is configured to direct operation of well system 101. Derrick 105 is located at a surface 106. Extending below derrick 105 is borehole 110 in which drill string 115 is inserted. Located at the bottom of drill string 115 is a downhole tool 120. Downhole tool 120 can include various bottom hole and downhole devices, such as a bottom hole assembly (BHA) and a drill bit 122. The drilling mud can be affected and altered by various materials and fluids, the environment, and by surrounding subterranean formation 130.

A drilling mud composition system 124 can be included with the surface equipment, such as proximate the well sit controller 107. Drilling mud composition system 124 includes a drilling mud extraction device, a dilution liquid dispenser, a mud container, an agitator, a probe, a mud composition controller, and optionally, a transceiver. Per a well system job plan or instructions from a well operator or engineer, drilling mud composition system 124 can extract drilling mud from other well system components and store it in the mud container, where thermal conductivity tests can be performed.

Drilling mud composition system 124 can perform the ASG, OWR, and fractional component computations and predictions. Alternatively, the collected thermal conductivity parameters can be transmitted to other systems for processing. For example, the computations and predictions can be performed by a computing system located with well site controller 107. The computation and prediction results can be communicated by various means to well site controller 107. Well site controller 107 or well site operators, using the received data, can modify the well system job plan and modify the composition of the original mud pumped downhole to compensate for the alterations occurring downhole, such as using the results to direct surface treatment methods, for example, centrifuges, shakers, and hydro cyclones.

Although FIG. 1 depicts a specific borehole configuration, those skilled in the art will understand that the disclosure is equally well suited for use in boreholes having other orientations including vertical boreholes, horizontal boreholes, slanted boreholes, multilateral boreholes, and other borehole types. FIG. 1 depicts an onshore operation. Those skilled in the art will understand that the disclosure is equally well suited for use in offshore operations.

FIG. 2 is an illustration of a diagram of an example schematic functional view of a mud composition measurement system 200. Mud composition measurement system 200 can receive a mud 220, measure thermal conductivity of mud 220, and compute composition information of mud 220 or communicate the thermal conductivity parameters to another system for the computation. Mud composition measurement system 200 is a functional view of processes used and is not intended to be a practical view perspective. Mud composition measurement system 200 includes a mud container 210, an agitator 212, and a probe 214.

Mud 220 can be drilling mud, and other operational usage types of mud. Mud 220 can be an OBM or a WBM, and can be altered by materials, processes, and environmental factors downhole, thereby becoming an altered mud. Mud 220 can be pumped into mud container 210 by a mud extractor, e.g., a pump capable of pumping mud from the active mud pit, flow line, or from within the borehole to mud container 210. The flow line into mud container 210 is shown as the 'borehole mud' line in mud composition measurement system 200, though the mud can be collected from a non-borehole location, for example, a surface storage tank. Mud container 210 can be located at or near the surface of the borehole, or in a laboratory environment. Mud container 210 can be pressurized and thermal conditioned to minimize the thermal conductivity measurement error.

Thermal conductivity parameters can be calculated using probe 214. Probe 214 can use various conventional devices, such as a transient hot wire, transient plane, and time-domain thermoreflectance devices and their associated algorithms. Probe 214 is shown upright in mud container 210. In alternate aspects, probe 214 can be located in various positions and orientations to mud container 210. In another aspect, one or more additional probes can be utilized for the thermal conductivity measurements.

Dilution liquid can be pumped into mud container 210 by a dilution liquid dispenser. The dilution liquid dispenser can include storage of one or more types of dilution liquids and can be able to dispense a known and measured amount of dilution liquid into mud container 210, so that the volume of fluid in mud container 210 is accurately known. The dilution liquid can be dispensed at a rate of approximately 2.5% to 30.0% by volume. The percent volume of dilution liquid needs to be enough to make a difference in the thermal conductivity measurements while not adversely altering the immersion by introducing an excess amount of dilution liquid. The dilution liquid can be a base oil, water, or other dilution liquids or liquid suspensions, such as HGS and LGS. Water, as a dilution liquid, can be one or more of various water compositions, such as distilled water, filtered water, ground water, brine, salinized, and water with other additives. In an alternative aspect, different dilution liquids can be used at the same time, such as adding base oil and water to mud 220, or adding base oil and a HGS to mud 220. Other combinations are also possible.

Agitator 212 can mix the dilution liquid and mud 220 to approximately homogenize the mixture in mud container 210 to form a diluted mud. Agitator 212 should operate for a minimum amount of time to homogenize the mixture. Continuing to agitate mud 220 past the point of homogenization can unnecessarily increase the thermal energy of mud 220, thereby altering the results of probe 214. Depending on the consistency of mud 220 and the dilution liquids utilized, the amount of operation time for agitator 212 can vary. In different examples, an average or typical agitator 212 operation time can be defaulted to a maximum of two minutes. A lesser operation time of agitator 212 can yield more accurate results if the mixture is homogenized in that lesser operation time.

Thermal conductivity measurements can be conducted again by probe 214. The new thermal conductivity parameters can be used, in conjunction with the previous set of thermal conductivity parameters, to compute the composition of mud 220 by a mud analyzer. The mud analyzer can be part of probe 214, be part of mud container 210, be part of another system located proximate mud container 210, or be part of the well site controller. The mud analyzer can utilize one or more of the Equations 1-7 in its processing.

The composition of mud 220 can include the OWR and ASG for oil-based muds, and the ASG for water-based muds. In other aspects, fractional components of the composition of mud 220 can be computed, such as the amount or ratios of base oil, water, HGS, and LGS. This information can be communicated to other systems by the mud analyzer, such as to a well site controller to be utilized to adjust the well system job plan or the composition of the original mud pumped into the downhole location.

Mud container 210 includes an outlet 216 to empty the contents when the testing has been completed. Mud composition measurement system 200 can be utilized repeatedly thereby reducing well system operation costs. In an alternative aspect, another mud container, such as or similar to mud container 210, can be located proximate to and used with mud container 210. Mud container 210 can receive the dilution liquid and both of the mud containers can receive mud 220. This aspect allows for the near simultaneous thermal conductivity testing of mud 220 in the containers, i.e., the mud in one container and the diluted mud in the other container. Conducting the two thermal conductivity tests in near simultaneous time frames, e.g., near parallel time frames, can reduce the time to conduct the tests thereby improving the overall efficiency of the operations of the well system. In addition, the mud composition determination process can be fully automated.

FIG. 3 is an illustration of a flow diagram of an example method 301 for determining the composition of a mud extracted from a borehole. Method 301 starts at a step 305 and proceeds to a step 310. In step 310, altered mud is extracted from the well system at one or more locations, for example, the returning mud after the shale shaker, the mud pit, and the pumping line before entering the borehole. The extraction can be completed by a pump that samples the altered mud and delivers it to a mud container. Alternatively, step 310 can extract mud from a surface location, such as a surface storage tank, line, or pipe prior to the mud being pumped into the borehole. The mud extractor and mud container can be proximate or separate from each other at a surface location.

In a step 315, a thermal conductivity of the extracted mud is measured, such as by using Equation 1B, or, alternatively, obtained for a portion of the mud. The thermal conductivity can be measured by one or more of various types of probes and used with a thermal conductivity algorithm to calculate the first thermal conductivity parameter, for example, a Maxwell thermal conductivity model can be utilized for the thermal conductivity algorithm. The mud can be placed in a mud container and the probe or probes can be inserted into the mud to obtain the measurements. In a step 318, a first thermal conductivity parameter can be calculated using the obtained thermal conductivity measurements.

In a step 320, a diluted mud is created by mixing a dilution liquid with the mud. A dilution liquid dispenser can dispense a known measured amount of the dilution liquid into the mud in a mud container. The dilution liquid dispensed can be one or more dilution liquids or other materials, for example, dispensing base oil and water into the extracted mud. An agitator can mix the mud and the dilution liquid to create the diluted mud. The mixing should be a time interval sufficient to homogenize the diluted mud. Continuing the mixing process past this point can introduce an excess of thermal energy into the diluted mud which can negatively affect the thermal conductivity measurements.

In a step 325, a second thermal conductivity is measured from the diluted mud, such as by using Equation 4. In an alternate aspect, steps 320 and 325 can be repeated using different dilution liquids. For example, in a first execution, the dilution liquid can be one of base oil or water. After step 325 is completed, step 320 can be repeated using the other of the base oil or water. Step 325 then can combine the second thermal conductivity parameter calculated in the first and second executions of step 325 and provide the combined second thermal conductivity parameter for further analysis.

In an alternate aspect, method 301 can employ two mud containers, each with a probe. One of the mud containers can include the dilution liquid dispenser and the agitator. This arrangement of components allows for steps 315/318 and steps 320/325 to be performed in approximately near simultaneous or parallel time frames to improve the response time of method 301.

In a step 330, various mud composition parameters are computed. For oil-based muds, the OWR and the ASG can be determined, such as by using Equations 6 and 7. For water-based muds, the ASG can be determined, such as by using Equation 7. In addition, the fractional components of the mud can be predicted, such as the fractional amounts or ratios of base oil, water, LGS, and HGS, such as by using Equations 2, 3, and 5. Method 301 ends at a step 350.

FIG. 4 is an illustration of a block diagram of an example mud composition system 400. Mud composition system 400 can be used to determine the composition of borehole mud, including the OWR, ASG, and fractional component amounts of the base oil, water, LGS, and HGS of the mud. Mud composition system 400 includes a well site controller 410 communicatively connected to a mud composition tool 430.

In some aspects, well site controller 410 can include a mud analyzer 412. Mud analyzer 412 can be utilized to compute the mud composition when the thermal conductivity parameters are received by the well site controller 410.

Mud composition tool 430 includes a mud extractor 432, a mud container 434, a dilution liquid dispenser 436, an agitator 438, a probe 440, and a mud tool controller 442. Optionally, a transceiver 444 can also be included. In an alternative aspect, optional components second probe 452 and second mud container 450 can be included, as shown by the dashed boxes. Mud composition tool 430 is shown using a dash-dot pattern to indicate that this is a functional view of the features used and an implementation of the functions can be grouped differently. For example, mud extractor 432 can be part of another well site system, and mud composition tool 430 can share the transceiver 444 with other well site systems.

Mud extractor 432 can pump a known measured amount of mud from the well system environment and borehole environment, for example, the mud pit, the flow lines, and other mud related systems, into mud container 434. Probe 440 can be utilized to measure the thermal conductivity and to calculate the thermal conductivity parameter for the mud in mud container 434. Next, dilution liquid dispenser 436 can dispense a known measured amount of dilution liquid into mud container 434. Agitator 438 is utilized to mix the mud and the dilution liquid to create a homogenized mixture. Probe 440 can be used again to measure the thermal conductivity and to calculate the thermal conductivity parameter of the now diluted mud.

In some aspects, dilution liquid dispenser 436 can dispense one or more dilution liquids at one time, and in some aspects, the process can be executed multiple times with a different set of dilution liquids in each execution. In another aspect, multiple mud containers can be part of mud composition tool 430, such as including second mud container 450 and second probe 452. This can allow the thermal conductivity parameters to be calculated for different muds, such as the mud in a first mud container and the diluted mud in a second mud container. The processes can operate in near simultaneous or parallel time frames thereby reducing the time to compute the mud composition.

Mud tool controller 442 can control the process and direct the operations of mud extractor 432, mud container 434, dilution liquid dispenser 436, probe 440, and agitator 438. When transceiver 444 is present, mud tool controller 442 can also direct the operations of transceiver 444. Mud tool controller 442 can store the thermal conductivity parameters for each respective measurement taken over time in a data store, such as a memory, a hard disk, a solid-state hard disk, USB key and other storage mediums, using a database, file, and other storage structures. Mud tool controller 442 can also store the computed mud composition values, as well as store and use pre-computed thermal conductivity measurements from known mud formulations. Mud tool controller 442 can utilize the Equations 1-7 in performing its operations. All of the stored parameters and values can be transmitted to other systems, such as well site controller 410 utilizing the transceiver 444. In some aspects, mud tool controller 442 can communicate the thermal conductivity parameters to other systems for analyzation, such as mud analyzer 412, which can also use the Equations 1-7.

Mud composition tool 430 and its components describe a functional view of the operations. The functions can be implemented in various combinations. For example, transceiver 444 can communicate with other well site systems. Another example is mud extractor 432 can be part another well site system rather than mud composition tool 430. Other combinations of the functionality are possible as well.

A portion of the above-described apparatus, systems or methods may be embodied in or performed by various digital data processors or computers, wherein the computers are programmed or store executable programs of sequences of software instructions to perform one or more of the steps of the methods. The software instructions of such programs may represent algorithms and be encoded in machine-executable form on non-transitory digital data storage media, e.g., magnetic or optical disks, random-access memory (RAM), magnetic hard disks, flash memories, and/or read-only memory (ROM), to enable various types of digital data processors or computers to perform one, multiple or all of the steps of one or more of the above-described methods, or functions, systems or apparatuses described herein.

Portions of disclosed embodiments may relate to computer storage products with a non-transitory computer-readable medium that have program code thereon for performing various computer-implemented operations that embody a part of an apparatus, device or carry out the steps of a method set forth herein. Non-transitory used herein refers to all computer-readable media except for transitory, propagating signals. Examples of non-transitory computer-readable media include, but are not limited to: magnetic media such as hard disks, floppy disks, and magnetic tape; optical media such as CD-ROM disks; magneto-optical media such as floptical disks; and hardware devices that are specially configured to store and execute program code, such as ROM and RAM devices. Examples of program code include both machine code, such as produced by a compiler, and files containing higher level code that may be executed by the computer using an interpreter.

In interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Those skilled in the art to which this application relates will appreciate that other and further additions, deletions, substitutions and modifications may be made to the described embodiments. It is also to be understood that the terminology used herein is for the purpose of describing particular embodiments only, and is not intended to be limiting, since the scope of the present disclosure will be limited only by the claims. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, a limited number of the exemplary methods and materials are described herein.

It is noted that as used herein and in the appended claims, the singular forms "a", "an", and "the" include plural referents unless the context clearly dictates otherwise.

Aspects disclosed herein include:

A. A method to determine a composition of a mud in a well system, including: (1) obtaining a thermal conductivity measurement for a portion of the mud, (2) calculating a first thermal conductivity parameter, using the measurement of thermal conductivity for the portion of the mud, (3) creating a diluted mud by adding a dilution liquid to the portion of the mud, (4) calculating a second thermal conductivity parameter, using a measurement of thermal conductivity for the diluted mud, and (5) computing an ASG of the mud and a ratio of fractional components of the mud utilizing the first thermal conductivity parameter and the second thermal conductivity parameter.

B. A system to determine a composition of a mud from a well system, including: (1) a first mud container, operable to hold the mud from the well system, (2) a dilution liquid dispenser, operable to dispense a measured volume of dilution liquid into the first mud container to form a diluted mud, (3) an agitator, operable to homogenize the diluted mud, (4) a probe, operable to measure a first thermal conductivity of contents of the first mud container, and calculate a first thermal conductivity parameter using the measured first thermal conductivity, and (5) a mud tool controller, operable to communicate with the first mud container, the dilution liquid dispenser, the agitator, and the probe, and operable to compute an ASG of the mud and a ratio of the fractional components of the mud, utilizing the first thermal conductivity parameter.

C. A computer program product having a series of operating instructions stored on a non-transitory computer-readable medium that directs a data processing apparatus when executed thereby to perform operations to determine a composition of a mud within a borehole, the operations including: (1) calculating a first thermal conductivity parameter, using a measurement of thermal conductivity for a portion of the mud located, (2) calculating a second thermal conductivity parameter, using a measurement of thermal conductivity for a diluted mud, wherein the diluted mud is created by adding a dilution liquid to the portion of the mud, and (3) computing an ASG of the mud and a ratio of fractional components of the mud utilizing the first thermal conductivity parameter and the second thermal conductivity parameter.

Each of aspects A, B, and C can have one or more of the following additional elements in combination: Element 1: wherein the portion of the mud is a first portion located in a first mud container. Element 2: wherein the mud is an altered mud. Element 3: wherein the mud is an OBM and the computing further comprises computing an OWR. Element 4: wherein the dilution liquid is 2.5 to 30.0 percent by volume of the altered mud. Element 5: wherein the creating the diluted mud comprises mixing the dilution liquid with the portion of the mud wherein the mixing does not exceed a duration of ten minutes. Element 6: wherein the creating the diluted mud utilizes a second mud container containing a second portion of the mud. Element 7: wherein the calculating the first thermal conductivity parameter utilizes the second mud container, and the calculating the first thermal conductivity parameter and calculating the second thermal conductivity parameter are conducted at or near simultaneous time frames. Element 8: wherein the fractional components of the mud are one or more of a base oil, a water, a low-gravity solid, and a high-gravity solid. Element 9: wherein the dilution liquid is a base oil or water. Element 10: wherein the dilution liquid is a mixture of the base oil and the water. Element 11: further comprising the creating the diluted mud and the computing the second thermal conductivity parameter are executed a second time with the other dilution liquid. Element 12: wherein the computing the ASG and the ratio of fractional components utilizes the second thermal conductivity parameters calculated in the first and second executions of the calculating the ASG. Element 13: further including a transceiver, operable to receive instructions and to transmit data, and communicate with the mud tool controller. Element 14: wherein the mud is an OBM. Element 15: wherein the mud tool controller is operable to compute an OWR. Element 16: wherein the agitator does not exceed ten minutes of operation when homogenizing contents of the first mud container. Element 17: wherein the probe is one of a transient hot wire, transient plane, and a time-domain thermoreflectance device. Element 18: wherein the dilution liquid dispenser is further operable to dispense one or more of a base oil and water. Element 19: further including a second probe and a second mud container located proximate the first mud container. Element 20: wherein the second mud container is configured to hold a portion of the mud. Element 21: wherein the second probe is operable to measure a second thermal conductivity of contents of the second mud container and calculate a second thermal conductivity parameter using the measured second thermal conductivity. Element 22: wherein the mud tool controller utilizes the second thermal conductivity parameter. Element 23: wherein there are a first and a second portion of the mud, and the calculating the first thermal conductivity parameter utilizes the first portion of the mud and calculating the second thermal conductivity parameter utilizes the second portion of the mud. Element 24: wherein the calculating the first thermal conductivity parameter and calculating the second thermal conductivity parameter are conducted at or near simultaneous time frames.

What is claimed is:

1. A method to determine a composition of a mud in a well system, comprising:
    obtaining a thermal conductivity measurement for a portion of the mud;
    calculating a first thermal conductivity parameter, using the measurement of thermal conductivity for the portion of the mud;
    creating a diluted mud by adding a dilution liquid to the portion of the mud;
    calculating a second thermal conductivity parameter, using a measurement of thermal conductivity for the diluted mud; and
    computing an average specific gravity (ASG) of the mud and a ratio of fractional components of the mud utilizing the first thermal conductivity parameter and the second thermal conductivity parameter.

2. The method as recited in claim 1, wherein the mud is an oil-based mud (OBM) and the computing further comprises computing an oil water ratio (OWR).

3. The method as recited in claim 1, wherein the mud is an altered mud and the dilution liquid is 2.5 to 30.0 percent by volume of the altered mud.

4. The method as recited in claim 1, wherein the creating the diluted mud comprises mixing the dilution liquid with the portion of the mud wherein the mixing does not exceed a duration of ten minutes.

5. The method as recited in claim 1, wherein the portion of the mud is a first portion located in a first mud container and the creating the diluted mud utilizes a second mud container containing a second portion of the mud.

6. The method as recited in claim 5, wherein the calculating the first thermal conductivity parameter utilizes the second mud container, and the calculating the first thermal conductivity parameter and calculating the second thermal conductivity parameter are conducted at or near simultaneous time frames.

7. The method as recited in claim 1, wherein the fractional components of the mud are one or more of a base oil, a water, a low-gravity solid, and a high-gravity solid.

8. The method as recited in claim 1, wherein the dilution liquid is a base oil or a water.

9. The method as recited in claim 8, further comprising the creating the diluted mud and the computing the second thermal conductivity parameter are executed a second time with the other dilution liquid, wherein the computing the ASG and the ratio of fractional components utilizes the second thermal conductivity parameters calculated in the first and second executions of the calculating the ASG.

10. The method as recited in claim 1, wherein the dilution liquid is a mixture of a base oil and a water.

11. A system to determine a composition of a mud from a well system, comprising:
    a first mud container, operable to hold the mud from the well system;
    a dilution liquid dispenser, operable to dispense a measured volume of dilution liquid into the first mud container to form a diluted mud;
    an agitator, operable to homogenize the diluted mud;
    a probe, operable to measure a first thermal conductivity of contents of the first mud container, and calculate a first thermal conductivity parameter using the measured first thermal conductivity; and
    a mud tool controller, operable to communicate with the first mud container, the dilution liquid dispenser, the agitator, and the probe, and operable to compute an average specific gravity (ASG) of the mud and a ratio of the fractional components of the mud, utilizing the first thermal conductivity parameter.

12. The system as recited in claim 11, wherein the mud is an altered mud and further comprising:
    a transceiver, operable to receive instructions and to transmit data, and communicate with the mud tool controller.

13. The system as recited in claim 11, wherein the mud is an oil-based mud (OBM) and the mud tool controller is operable to compute an oil water ratio (OWR).

14. The system as recited in claim 11, wherein the agitator does not exceed ten minutes of operation when homogenizing contents of the first mud container.

15. The system as recited in claim 11, wherein the probe is one of a transient hot wire, transient plane, and a time-domain thermoreflectance device.

16. The system as recited in claim 11, wherein the dilution liquid dispenser is further operable to dispense one or more of a base oil and a water.

17. The system as recited in claim 11, further comprising a second probe and a second mud container located proximate the first mud container, wherein the second mud container is configured to hold a portion of the mud, and the second probe is operable to measure a second thermal conductivity of contents of the second mud container and calculate a second thermal conductivity parameter using the measured second thermal conductivity, further wherein the mud tool controller utilizes the second thermal conductivity parameter.

18. A computer program product having a series of operating instructions stored on a non-transitory computer-readable medium that directs a data processing apparatus when executed thereby to perform operations to determine a composition of a mud in a well system, the operations comprising:
    calculating a first thermal conductivity parameter, using a measurement of thermal conductivity for a portion of the mud;
    calculating a second thermal conductivity parameter, using a measurement of thermal conductivity for a diluted mud, wherein the diluted mud is created by adding a dilution liquid to the portion of the mud; and computing an average specific gravity (ASG) of the mud and a ratio of fractional components of the mud utilizing the first thermal conductivity parameter and the second thermal conductivity parameter.

19. The computer program product as recited in claim 18, wherein the mud is an oil-based mud (OBM) and the computing further comprises computing an oil water ratio (OWR).

20. The computer program product as recited in claim 18, wherein there are a first and second portion of the mud, and the calculating the first thermal conductivity parameter utilizes the first portion of the mud and calculating the second thermal conductivity parameter utilizes the second portion of the mud, and the calculating the first thermal conductivity parameter and calculating the second thermal conductivity parameter are conducted at or near simultaneous time frames.

\* \* \* \* \*